United States Patent [19]
Falk et al.

[11] Patent Number: 4,714,234
[45] Date of Patent: Dec. 22, 1987

[54] LOW POWER ELECTROMAGNETIC VALVE

[75] Inventors: Theodore J. Falk, Clarence; Lawrence E. Morris, Bowmansville, both of N.Y.

[73] Assignee: Greatbatch Enterprises, Inc., Clarence, N.Y.

[21] Appl. No.: 754,203

[22] Filed: Jul. 11, 1985

Related U.S. Application Data

[63] Continuation of Ser. No. 415,672, Sep. 9, 1982, abandoned.

[51] Int. Cl.$^4$ .............................................. F16K 31/04
[52] U.S. Cl. .......................... 251/129.17; 251/129.07; 251/335.2; 137/375; 604/249
[58] Field of Search ................ 137/375; 251/129, 141, 251/335 A, 129.17; 604/131, 245, 249, 891

[56] References Cited

U.S. PATENT DOCUMENTS

| | | | |
|---|---|---|---|
| 2,548,239 | 4/1951 | Ray | 251/141 |
| 2,820,604 | 1/1958 | Ray | 251/129 |
| 2,925,985 | 2/1960 | MacDavid | 251/141 |
| 3,235,223 | 2/1966 | Wintriss | 251/141 |
| 3,424,429 | 1/1969 | Monnich | 251/129 |
| 3,531,080 | 9/1970 | Dillon | 251/129 |
| 3,750,698 | 8/1973 | Walchle et al. | 137/375 |
| 3,937,242 | 2/1976 | Echert | 251/129 X |
| 3,942,759 | 3/1976 | Passera | 251/129 |
| 3,948,284 | 4/1976 | Walworth | 137/375 X |
| 4,102,526 | 7/1978 | Hargraves | 251/139 |
| 4,218,669 | 8/1980 | Hitchcock et al. | 251/129 X |
| 4,262,877 | 4/1981 | Lang | 251/141 |
| 4,399,834 | 8/1983 | Baumann | 137/375 |

FOREIGN PATENT DOCUMENTS 2205930 5/1974 France .
853469 11/1960 United Kingdom .

Primary Examiner—A. Michael Chambers
Assistant Examiner—John C. Fox
Attorney, Agent, or Firm—Christel, Bean & Linihan

[57] ABSTRACT

An electromagnetic valve comprising a housing having fluid containing region and first and second ports in communication therewith, an electromagnet carried by the housing located external to the region, and a thin fluid impermeable diaphragm barrier hermetically isolating the electromagnet from the region. An armature in the housing is movable within a body of magnetically permeable material and has a pole portion located for magnetic attraction by the electromagnet and has a valve portion located for opening and closing one of the ports to place the ports in fluid communication through the region in one state of the valve and to block fluid communication between the ports in another state of the valve. The armature is moved from a rest position through a forward stroke when attracted by the electromagnet and is returned by a biasing spring to the rest position. A magnetic circuit includes the electromagnet, a portion of the barrier, the body, the armature pole portion and a gap between the pole portion and the electromagnet located in the fluid containing region of the housing which gap is closed during forward movement of the armature. The valve is made electrically and magnetically efficient by minimizing the total gap within the magnetic circuit, by having the armature pole face area relatively large, and by having the electromagnet coil or core of relatively small diameter.

20 Claims, 8 Drawing Figures

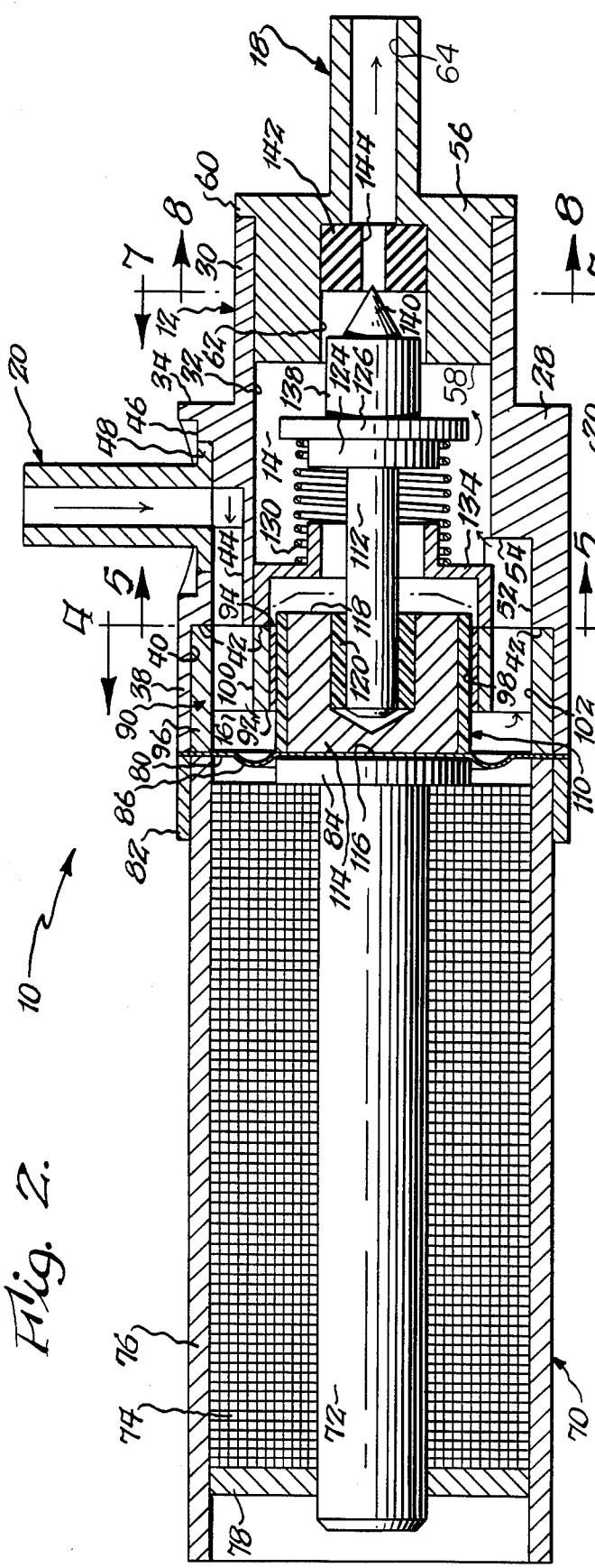
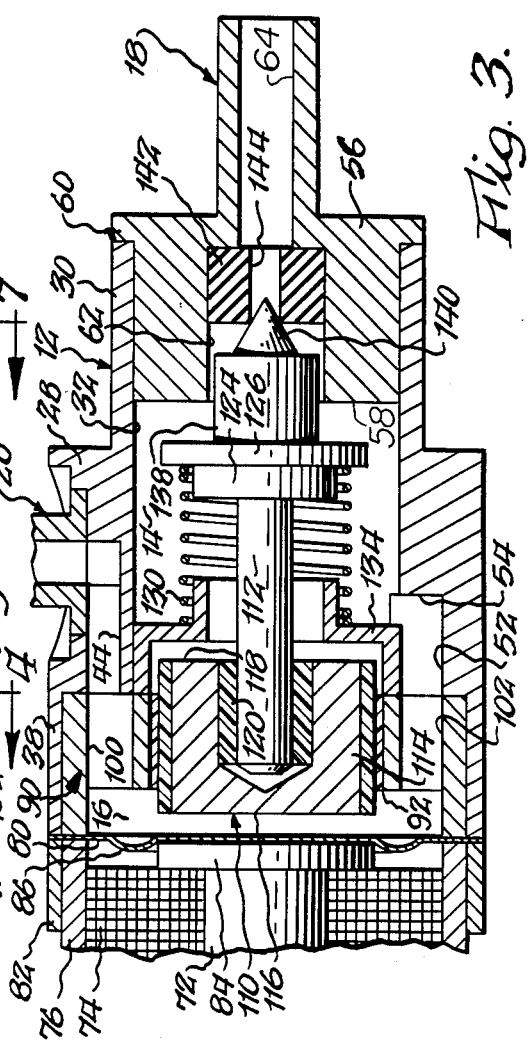

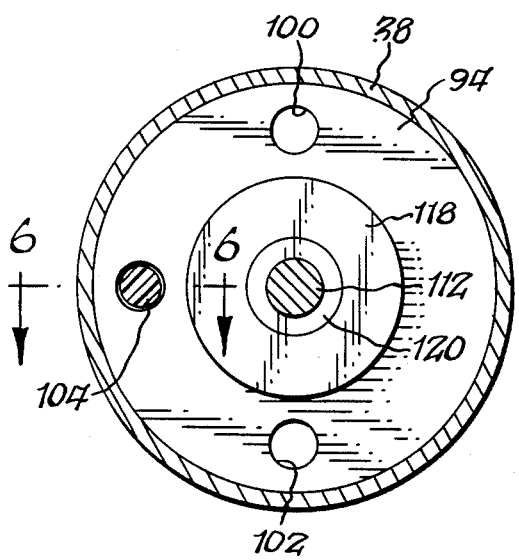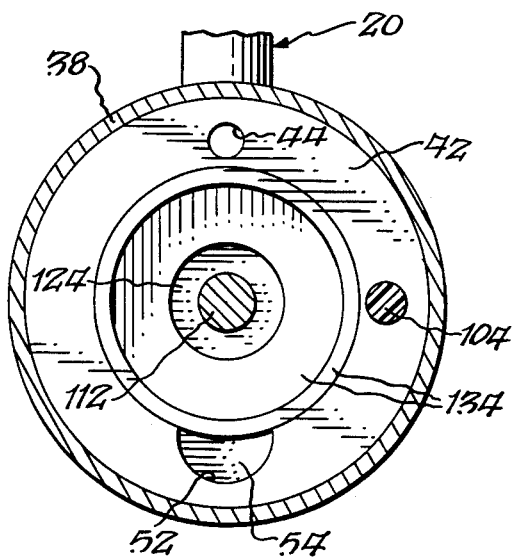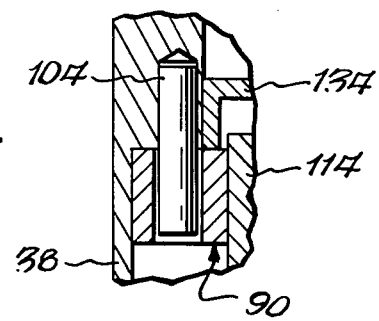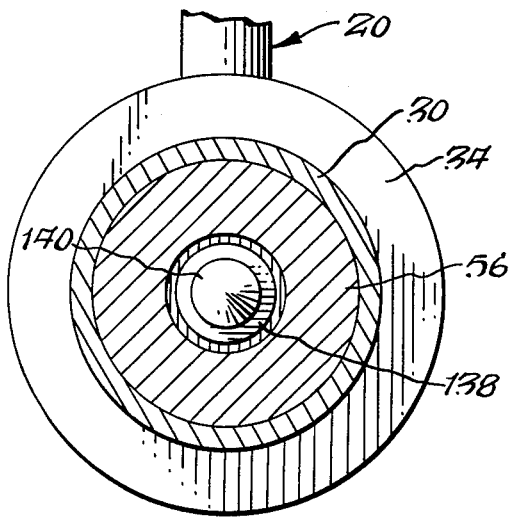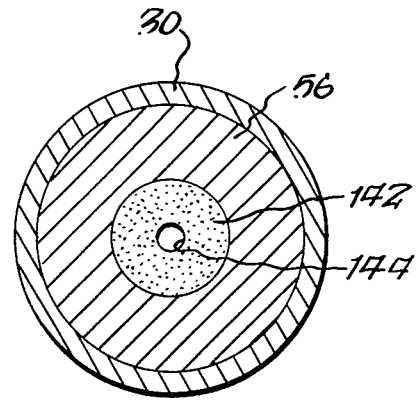

LOW POWER ELECTROMAGNETIC VALVE

This application is a continuation of application Ser. No. 415,672, filed Sept. 9, 1982 now abandoned.

BACKGROUND OF THE INVENTION

This invention relates to the art of electromagnetically-operated fluid valves, and more particularly to a new and improved electromagnetic valve which operates at extremely low power.

One area of use of the present invention is implantable drug delivery systems, although the principles of the present invention can be variously applied. The principal requirements for a valve in such applications are low power drain, since the valve must be driven by an implanted battery, and compatibility with the drug being handled. It would, therefore, be highly desirable to provide an electromagnetically-operated valve which is safe, reliable, small in size, light in weight, which operates without excessive demand on the available energy supply and which is compatible with drugs or similar liquids being handled.

SUMMARY OF THE INVENTION

It is, therefore, a primary object of this invention to provide a new and improved electromagnetically-operated valve.

It is a more particular object of this invention to provide such a valve which operates at extremely low power levels.

It is a further object of this invention to provide such a valve which is compatible with drugs and similar liquids being handled.

It is a more particular object of this invention to provide such a valve which is small in size, light in weight and reliable in operation.

It is a further object of this invention to provide such a valve which is electrically and magnetically efficient.

The present invention provides an electromagnetic valve comprising a housing having fluid containing region and first and second ports in communication with the region, electromagnet means carried by the housing located external to the fluid containing region of the housing, and barrier means in the form of a thin diaphragm of fluid impermeable material which hermetically isolates the electromagnet from the fluid chamber. An armature in the housing is movable within a body of magnetically permeable material and has a pole portion located for magnetic attraction by the electromagnet and has a valve portion located for opening and closing one of the ports to place the ports in fluid communication through the housing region in one control state of the valve and to block fluid communication between the ports through the housing region in another control state of the valve. The armature is moved from a rest position through a forward stroke when attracted by the electromagnet means to change the control state of the valve, and the armature is moved by biasing means in an opposite direction through a return stroke back to the rest position. A magnetic circuit is defined including the electromagnet means, a portion of the fluid-impermeable barrier, the body, the armature pole portion and a gap defined between the pole portion and the electromagnet and located in the fluid containing region of the housing and external to the electromagnet which gap is closed during movement of the armature toward the electromagnet during energization thereof. The valve is made electrically and magnetically efficient by minimizing the total gap within the magnetic circuit, by having the pole face area relatively large on the armature pole portion, and by having the electromagnet include a coil on a core of relatively small diameter.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 1 is a side elevational view of a valve according to the present invention;

FIG. 2 is an enlarged longitudinal sectional view, partly in elevation, of the valve of FIG. 1;

FIG. 3 is a fragmentary longitudinal view of the valve of FIG. 2 showing the armature in a rest position;

FIG. 4 is a sectional view taken about on line 4—4 in FIG. 2;

FIG. 5 is a sectional view taken about on line 5—5 in FIG. 2;

FIG. 6 is a fragmentary sectional view taken about on line 6—6 in FIG. 4;

FIG. 7 is a sectional view taken about on line 7—7 in FIG. 2; and

FIG. 8 is a sectional view taken about on line 8—8 in FIG. 2.

DETAILED DESCRIPTION OF THE ILLUSTRATED EMBODIMENT

Referring now to FIGS. 1-8, a valve 10 according to the present invention includes a housing 12 which is generally hollow cylindrical in overall shape and includes an interior region for containing fluid, i.e. the liquid to be delivered. As shown in FIG. 2, the hollow interior region is divided in a manner which will be described into a first chamber 14 and a second chamber 16 in fluid communication therewith. There is a first port generally designated 18 in fluid communication with the first chamber 14 and adapted to be connected in the fluid handling circuit. There is also a second port 20 in fluid communication with the second chamber 16 and adapted to be connected in the fluid handling circuit. In the illustrative valve shown, port 20 is connected to the relatively higher pressure portion of the fluid circuit, and port 18 is connected to the relatively lower pressure portion. Thus, port 20 may be viewed as the valve inlet and port 18 as the valve outlet.

Referring now to FIG. 2, housing 12 is generally hollow cylindrical in overall shape including a central body portion 28 of relatively substantial wall thickness. Housing 12 also includes a first axial end portion 30 extending from one end of body portion 28, i.e. the right-hand end as viewed in FIG. 2, and which is of relatively smaller wall thickness. Portions 28 and 30 define the interior region of constant diameter having an inner surface 32. Thus, the outer surfaces of portions 28 and 30 are of different diameters and meet in an annular surface 34. The housing 12 has a second axial end portion 38 extending from the other end of body 28, i.e. the left-hand end as viewed in FIG. 2, which also is of smaller wall thickness. End portion 38 has a relatively larger diameter inner wall surface 40 which meets surface 32 in annular intermediate wall 42.

Body portion 28 is provided with a longitudinal bore or passage 44 in the upper portion of wall 42 as viewed in FIG. 2 for placing chamber 16 in fluid communication with port 20. Port 20 is located on the side of housing 12 for communication with the passage 44. Housing portion 28 is provided with a radially extending opening in the outer wall thereof in communication with passage 44. The opening is formed to include an annular recess 46 defining a ledge which engages an annular rim 48 of a tubular fitting which defines the port 20. Body portion 28 also is provided with a recess 52 in the lower portion of wall 42 as viewed in FIG. 2 for placing chamber 16 in fluid communication with chamber 14. Recess 52 is generally semi-circular in shape and terminates in an inner wall 54 which, in turn, meets surface 32. Port 20 is adapted for connection to a conduit such as a flexible tubing comprising a portion of the fluid circuit.

Port 18 is provided by a plug-like element which is fitted into the open end of the housing axial end portion 30. The element includes a main body 56 generally cylindrical in shape and having an outer diameter substantially equal to the diameter of inner wall surface 32 thereby providing a close fit therein. Body 56 has one axial end face 58 located in chamber 14, and adjacent the opposite end face the outer surface of body 56 is provided with an annular rim 60 which abuts the annular end face of housing portion 30 for placement and securement of the fitting in the housing. The two components are secured together by welding or other suitable means. The body portion 56 has an internal wall surface 62 defining a region of substantial diameter. The port 18 is defined by a relatively smaller diameter portion of the plug element having an internal passage 64 of relatively smaller diameter compared to passage 62. Port 18 is adapted for connection to a conduit such as a flexible tubing forming a portion of the fluid circuit.

By way of example, in an illustrative valve, housing 12 and the port fittings 18 and 20 all are of metal, and for a drug delivery pump for implantation in a patient, titanium has been found to provide satisfactory results. In such an illustrative valve, housing 12 has an overall length of about 0.385 inch measured between the axial end faces of portions 30 and 38. Surface 32 has a diameter of about 0.170 inch, and the axial end face of portion 30 has a radial dimension of about 0.030 inch. Surface 40 has a diameter of about 0.260 inch, and the axial end face of housing portion 38 has a radial thickness of about 0.020 inch. Passage 44 in housing body 28 and the interior passage in port fitting 20 both have a diameter of about 0.020 inch. In the port fitting 18, the passage 62 has a diameter of about 0.073 inch and passage 64 has a diameter of about 0.032 inch.

The valve of the present invention further comprises electromagnet means generally designated 70 carried by housing 12 and located external to the fluid containing region of the housing. As shown in FIG. 2, the electromagnet 70 includes a core 72 in the form of a spool which is generally solid cylindrical in shape. A coil 74 is wound on spool 72 and contained within a hollow housing 76 generally cylindrical in shape. One end of electromagnet 70 is adjacent and in abutting relation to housing 12, and the opposite end, i.e. the left-hand end as viewed in FIG. 2, is closed by a plate element 78 fitted within the open end of housing 76 and fitted onto an end of spool 72. Electromagnet 70 is joined to housing 12 in the following manner.

The interior, fluid containing region of housing 12 and the electromagnet 70 are separated by a barrier means of fluid impervious material in the form of a relatively thin plate or diaphragm-like component 80. The end of magnet housing 76 adjacent housing 12 is provided with an annular band 82 around the outer surface and adjacent the axial end face of housing 76. The outer diameter of band 82 when placed on housing 76 is substantially equal to the outer diameter of housing portion 38 so that the respective outer surfaces are substantially flush. The axial end faces of band 82 and magnet housing 76 are coplanar. The housing and electromagnet structures are placed in abutting relation on opposite surface portions of the plate 80, and the assembly secured together by a weld joining the respective adjacent outer surfaces of band 82 and housing portion 38. In addition, an enlarged annular end portion 84 of spool 72 contacts the central portion of plate 80 in a manner supporting the same. Plate 80 is formed with an annular groove or depression 86 in the surface facing magnet 70 and having an inner diameter substantially equal to the outer diameter of spool end 84 to receive end 84 therein and strengthen plate 80.

By way of example, in an illustrative valve, spool 72, magnet housing 76 and closure 78 are of ferromagnetic material, for example 0.4750 nickel iron alloy. Plate 80 and band 82 are of titanium, the mateiral of plate 80 being found suitable for use in the exemplary implanted drug delivery pump previously mentioned. Spool 72 has a length of about 0.555 inch and a diameter of 0.079 inch. Housing 76 has a wall thickness of about 0.03 inch, band 82 a thickness of about 0.02 inch and diaphragm 80 a thickness of about 0.001 inch. Coil 74 is about 7600 turns of 45 gauge wire.

The valve of the present invention further comprises a body 90 of magnetically permeable material in the fluid containing region of housing 12 and between the first and second chambers 14 and 16, respectively. In addition to defining portions of the two chambers, body 90 also defines a portion of the magnetic circuit in the valve, along with other components of the valve, in a manner which will be described. Body 90 is generally solid cylindrical in shape having an outer diameter substantially equal to the diameter of housing inner surface 40 thereby providing a close fitting relationship. Body 90 has a main body portion between axial end surfaces 92 and 94 which is of an axial length less than the distance between housing surface 42 and plate 80 by an amount determined by the desired dimension of chamber 16. Body 90 is formed to include an outer annular rim portion 96 extending from end face 92 and which abuts a corresponding surface portion of plate 80 as shown in FIG. 2. The radial thickness of rim portion 96 is substantially equal to that of magnet housing 76, and the two are in substantial alignment for maximizing transmission of magnetic flux therebetween in a manner which will be described. Body 90 is provided with a central through bore or passage 98 of substantial diameter for receiving a portion of the valve armature in a manner which will be described. The main portion of body 90 also is provided with a first, smaller through bore or passage 100 offset from passage 98 and of substantially the same diameter and in registry with outlet passage 44 thereby providing fluid communication between chamber 16 and port 20. There is a second, small through bore or passage 102 offset from passage 98 and in communication with recess 52 thereby providing fluid communication between chamber 16 and chamber 14. Body 90 is positioned in housing 12 by means of a rod 104 extending through corresponding bores in body 90 and valve housing portion 28 shown in FIGS. 4-6, the bolt 104 preferably being of Teflon material and the parts being secured together by a compression fit.

By way of example, in an illustrative valve, body 90 is of mu metal which is selected to provide the desired degree of magnetic permeability while at the same time being compatible with medicine or the like for use in the exemplary implanted drug delivery valve previously mentioned. As is well known, mu metal includes nickel in a major portion with the balance including iron, copper and chromium. In addition some or all of the external surfaces of body 90 can be plated or coated with gold or some other suitable material chosen to enhance the compatibility of the drug with the external surfaces. The outer diameter of body 90 is about 0.260 inch, the axial length between end face 94 and the end face of rim 96 is about 0.090 inch, and the axial length between end faces 92,94 is about 0.060 inch. Passage 100 has a diameter of about 0.029 inch, central passage 102 has a diameter of about 0.029 inch.

The valve according to the present invention further comprises an armature generally designated 110 positioned in the fluid containing region of housing 12. The armature has a pole portion located for magnetic attraction by the electromagnet 70, a plunger portion in the chamber 16, and a valve portion located for opening and closing port 18. The armature 110 is movably supported in housing 12 for movement from a rest position through a forward stroke when attracted by the electromagnet 70 to open port 18 and place the ports 18,20 in fluid communication through the chambers 14,16 and for movement in an opposite direction through a return stroke back to the rest position closing port 18 and blocking fluid communication between ports 18,20 through chambers 14,16. In FIG. 2, armature 110 is shown in a position at the end of the forward stroke in response to energization of electromagnet 70, and in FIG. 3 armature 110 is shown in the rest position at the end of the return stroke which will be described in detail presently.

Armature 110 includes a shaft or rod portion 112 which is positioned in housing 12 with the longitudinal axis thereof generally coincident with the longitudinal axis of housing 12. A major portion of the length is a section of relatively small diameter. The armature further includes an enlarged body portion 114 of magnetically permeable material which provides the armature pole portion and the plunger portion in a manner which will be described. Body 114 is solid cylindrical in shape having an outer diameter slightly smaller than the diameter of passage 98 in body 90. This is to allow reciprocal movement of armature body 114 within the body 90 during the forward and return strokes of armature 110. The armature body 114 terminates at the end facing electromagnet 70 in an axial end face 116 which serves as the pole face and is disposed substantially perpendicular to the armature axis. The pole face 116 together with electromagnet 70 define the magnetic circuit gap which is closed during the forward armature stroke. The pole face 116 is of relatively large cross-sectional area as compared to the cross sectional area of the armature shaft portion 112. The body 114 also serves as the plunger portion of the armature, and as the pole face 116 moves toward plate 80 during the forward stroke when magnet 70 is energized, body 114 upon moving into chamber 16 displaces fluid therefrom forcing it out through passages 102,52 to chamber 14.

Shaft portion 112 is fixed to body 114 in the following manner. Body 114 is provided with a longitudinal bore extending inwardly from the opposite axial end face 118 which terminates within body 114 at a location spaced from pole face 116. A sleeve 120 of fluoropolymer material such as Teflon is fitted in the bore, and the end of the armature shaft portion 112 is fixed in the sleeve or bushing 120. The foregoing is provided by a mechanical compression fit.

Armature 110 includes two relatively larger diameter shaft sections spaced axially from body 114 in a direction opposite therefrom. In particular, there is a first section 124 facing body 114 and a second, axially adjacent section 126 which of slightly larger diameter. The two sections 124,126 are of relatively short axial length, and they define therebetween an annular shoulder facing the body 114.

There is also provided biasing means in the form of a coil spring 130 for urging armature 110 toward the rest position shown in FIG. 3. One end of spring 130 seats in the annular shoulder defined by the armature shaft sections 124,126. The opposite end of spring 130 seats in an annular spring retainer element 134 which has an annular rim portion which abuts against the end face 94 of body 90 as shown in FIG. 2. The annular shape of retainer 134, with the two diameter rim sections, enables it to be located concentric with the armature shaft section 112 to receive the spring 130 which also is concentric with the shaft, while at the same time not interfering with body 114 during movement of the armature 110. The outer diameter of the largest rim portion of retainer 134 is substantially less than the diameter of surface 32, and retainer 134 is merely located within the housing 12, being held in place by the force of spring 130.

Armature 110 has a valve portion at the axial end of the armature opposite that of the pole face 116 for closing the port 18 when the armature is in the rest position and for opening port 18 when the armature is moved during the forward pumping stroke. There is provided an armature shaft section 138 having an outer diameter slightly less than the diameter of passage 62 in body 56. Section 138 terminates in a conical tip formation 140 at the axial end of the armature. The tip 140 is adapted for movement into and out of seating engagement with a body 142 fitted in passage 62 and having a longitudinal passage 144 therein in communication with port passage 64. In particular, the surface of cone 140 contacts the edge of opening 114 during seating of the valve to block fluid communication between port 18 and chamber 14. In the device shown, passage 144 is of smaller diameter than passage 64. The tip 140 is of metal and the element 142 is of relatively soft material, for example silicone rubber, to facilitate the seating of element 140 therein.

By way of example, in an illustrative pump, the armature rod or shaft portion including the sections 112, 124, 126, 138 and 140 is machined from metal, preferably titanium for use in the aforementioned illustrative implanted drug delivery valve. Armature body 114 is of mu-metal, retainer 134 is of titanium and body 142 can be cut from a length of silicone rubber tubing. In addition, armature body 114 can be coated or plated with gold, or other suitable material, like body 90, chosen to enhance the compatibility of the drug with the external surface. Also, the outer surface of body 114 received in passage 98 can be coated with Teflon to reduce friction. The armature shaft or rod portion has an overall length of about 0.305 inch from the end fitted within body 114 to the end of the conical tip 140. The smaller diameter section 112 of major axial length has a diameter of about 0.036 inch, and the relatively larger diameter sections 124 and 126 have diameters of about 0.093 and 0.136 inch, respectively, and axial lengths of about 0.035 and 0.015 inch, respectively. Section 138 has a diameter of about 0.068 inch and a length of about 0.058 inch, and conical tip 140 has an axial length of about 0.037 inch and a base angle of about 60°, Body 114 has an overall axial length of about 0.100 inch and an outer diameter of about 0.137 inch. Spring 130 is 0.006 titanium wire and the passage 144 in body 142 has a diameter of about 0.015 inch.

In operation, port 18 is connected to an appropriate location in the relatively lower pressure portion of a fluid circuit, and port 20 is connected to a location in the higher pressure portion of the circuit. The armature 110 is moved through the forward stroke in response to electrical energization of electromagnet 70. One way of energizing magnet 70 is to charge a capacitor from a battery and then discharge that capacitor through coil 74. Other procedures can of course be employed for electrically energizing coil 74 in a known manner. Prior to electrical energization of magnet 70, armature 110 is in the rest position illustrated in FIG. 3 where the valve at the end of armature 110 in the form of conical tip 140 is seated in opening 144 to block fluid communication between port 18 and chamber 14. In the rest position of armature 110, pole face 116 is spaced from diaphragm 80 as shown in FIG. 3 thereby defining the gap in the magnetic circuit. In the rest position this gap between pole face 116 and diaphragm 80 is of maximum length.

When coil 74 is electrically energized, the armature pole portion 114 is attracted toward magnet 70 thereby causing armature 110 to be drawn toward diaphragm 80. Electromagnetic flux travels through the magnetic circuit including the electromagnet core 72, plate 78, magnet housing 76, rim 96 of body 90, the included portion of diaphragm 80 between housing 76 and rim 96, body 90, armature pole portion 114, and the gap between pole face 116 and diaphragm 80. As armature 110 is moved in the forward stroke, i.e. in a direction to the left as viewed in FIGS. 2 and 3, the armature pole portion 114 moves further into chamber 16, armature pole face 116 moves closer to diaphragm 80 thereby decreasing the gap in the magnetic circuit, and conical surface 140 becomes unseated from the opening of passage 144 thereby placing port 18, chambers 14,16 and port 20 in fluid communication. Fluid thus flows as indicated by the arrows in FIG. 2 from port 20, through passages 44,100 into chamber 16, from chamber 16 through passages 102,52 into chamber 14 and from chamber 14 out through port 18. The forward stroke of armature 110 is completed when pole face 116 approaches contact with diaphragm 80. Acutal contact may not be achieved since viscosity limits outlfow of the fluid between the pole face 116 and diaphragm 80.

When electrical excitation of coil 74 ceases, armature 110 is moved in the opposite direction i.e. to the right as viewed in FIGS. 2 and 3, by the force of biasing spring 130 until the armature reaches the rest position as shown in FIG. 3 with conical tip 140 seated in the opening of passage 144. Armature 110 then remains in the rest position of FIG. 3 closing port 18 and waiting for the next forward stroke which occurs when magnet 70 is energized again. In the illustrative mode wherein coil 74 is excited by the discharge of a capacitor therethrough, the time during which valve 10 places ports 18,20 in communication, i.e. the time during which valve 10 is open, is relatively short. However, having the valve open for such a relatively short time is called for in typical implantable drug dosage delivery systems. Alternatively, valve 10 can be held open for whatever longer duration may be desired simply by continuing the energization of magnet 70.

The non-movable diaphragm 80 of titanium or like material provides an hermetic seal between the fluid in housing 12 and the electrical components associated with magnet 70. Having armature 110 immersed in the fluid makes operation of the valve nearly independent of ambient pressure. The initial condition of the valve when armature 110 is in the rest position of FIG. 3 is that the fluid is at substantially the same pressure on opposite sides of the pole portion 114, i.e. in the two chambers 14 and 16.

The valve of the present invention is made electrically and magnetically efficient by minimizing the total gap within the magnetic circuit, by having the magnetic pole face 116 of relatively large surface area, and by having core 72 of relatively small diameter. In particular, there is a relatively large contact area at the interface between the axial end face of magnet housing 76 and diaphragm 80 and between diaphragm 80 and the axial end face of rim 96 of body 90 to minimize the effective air gap introduced by diaphragm 80 at this point in the magnetic circuit. Related to this is the need for welding diaphragm 80 to the band 82 and housing part 38 to achieve an hermetic seal between electromagnet 70 and the fluid containing region of housing 12 while at the same time not adversely affecting the magnetic circuit. In addition, there is a relatively large surface area along the gap between body 90 and pole portion 114 to minimize the effective air gap introduced at this point in the magnetic circuit. The relatively small diameter of core 72 provides the necessary ampere turns with a minimum electrical resistance. The large area of pole face 116 provides a high magnetic force with a minimum number of ampere turns. Having the magnetic gap external to coil 74, i.e. between pole face 116 and diaphragm 80, allows the foregoing features to be achieved simultaneously. The external Teflon coating over the gold plating on pole portion 114 reduces magnetic side loading on armature pole portion 114 and reduces operating friction. The combination of the conical formation 140 and the relatively soft body 142 enables the armature 110 to be self-aligning and permits relatively loose tolerance in construction. The valve of the present invention is small in size having an overall diameter of aroung 7 millimeters and an overall length of about 25 millimeters, and has the relatively light weight of about 4.25 grams. A valve of the present invention as described hereinabove can be opened with an initial power drain of between about 6 and 10 milliwatts and held open with less than about 2 milliwatts power drain thereby operating at exceptionally low power levels.

The valve of the present invention is illustrated further by the following example and data. A valve as shown in FIGS. 1–8 was pulsed to a valve open condition by a 3.3 microfarad capacitor at 9 volts to pass 2.4 microliters per pulse at a pressure difference across the valve of 5 p.s.i. At a 1 milliliter per day flow rate (417 pulses per day) the calculated five year energy requirement from the capacitor is 102 joules. This is less than about ½% of the energy available from a model 7911 lithium-iodine cell commercially avaialbe from Wilson Greatbatch Ltd., Clarence, N.Y.

Tables I, II and III present performance data obtained from operating a valve as shown in FIGS. 1–8 with water, a coil resistance of about 1 kilohm, 5 psi. pressure difference across the valve, and capacitor magnitudes of 1.5, 3.3 and 4.7 microfarads, respectively:

TABLE I

Volume Delivered Per Pulse vs. Capacitor Voltage
Capacitance of 1.5 Microfarads

| Initial Capacitor Voltage In Volts | Volume Delivered Per Pulse In Microliters |
|---|---|
| 8.5 | 0 |
| 9.0 | 0.4 |
| 9.5 | 0.8 |
| 10.0 | 1.1 |
| 10.5 | 1.3 |
| 11.0 | 1.6 |
| 11.5 | 1.7 |
| 12.0 | 1.8 |
| 12.5 | 2.0 |
| 13.0 | 2.2 |
| 13.5 | 2.3 |

TABLE II

Volume Delivered Per Pulse vs. Capacitor Voltage
Capacitance of 3.3 Microfarads

| Initial Capacitor Voltage In Volts | Voltage Delivered Per Pulse In Microliters |
|---|---|
| 6.5 | 0.7 |
| 7.0 | 1.3 |
| 7.5 | 1.7 |
| 8.0 | 2.0 |
| 8.5 | 2.2 |
| 9.0 | 2.4 |
| 10.0 | 2.7 |
| 10.5 | 2.8 |
| 11.0 | 2.9 |
| 12.0 | 3.3 |
| 13.0 | 3.3 |

TABLE III

Volume Delivered Per Pulse vs. Capacitor Voltage
Capacitance Voltage of 4.7 Microfarads

| Initial Capacitor Voltage In Volts | Voltage Delivered Per Pulse In Microliters |
|---|---|
| 6.0 | 1.3 |
| 6.5 | 1.9 |
| 7.0 | 2.2 |
| 7.5 | 2.6 |
| 8.0 | 2.9 |
| 8.5 | 3.2 |
| 9.0 | 3.6 |
| 9.5 | 3.6 |
| 10.0 | 3.8 |
| 10.5 | 3.8 |
| 11.0 | 3.8 |
| 11.5 | 3.9 |
| 12.0 | 4.0 |
| 12.5 | 4.0 |
| 13.0 | 4.2 |

Tables IV, V and VI present performance data obtained from operating a valve as shown in FIGS. 1–8 with water, a coil resistance of about 1 kilohm, 5 psi. pressure difference across the valve, and capacitor magnitudes of 1.5, 3.3 and 4.7 microfarads, respectively.

TABLE IV

Capacitor Energy Per Milliliter Delivered
Capacitance of 1.5 Microfarads

| Volume Delivered Per Pulse (Microliters/Pulse) | Energy Per ML Delivered (Joules/Milliliters) |
|---|---|
| 0.4 | 0.145 |
| 0.7 | 0.100 |
| 0.8 | 0.080 |
| 1.1 | 0.070 |
| 1.3 | 0.060 |
| 1.6 | 0.055 |
| 2.0 | 0.060 |
| 2.2 | 0.060 |

TABLE V

Capacitor Energy Per Milliliter Delivered
Capacitance of 3.3 Microfarads

| Volume Delivered Per Pulse (Microliters/Pulse) | Energy Per ML Delivered (Joules/Milliliter) |
|---|---|
| 0.7 | 0.120 |
| 0.9 | 0.080 |
| 1.2 | 0.065 |
| 1.4 | 0.060 |
| 1.6 | 0.055 |
| 1.8 | 0.050 |
| 2.0 | 0.050 |
| 2.3 | 0.055 |
| 2.4 | 0.055 |
| 2.7 | 0.060 |
| 2.9 | 0.070 |
| 3.3 | 0.080 |

TABLE IV

Capacitor Energy Per Milliliter Delivered
Capacitance of 4.7 Microfarads

| Volume Delivered Per Pulse (Microliters/Pulse) | Energy Per ML Delivered (Joules/Milliliter) |
|---|---|
| 0.5 | 0.150 |
| 1.2 | 0.070 |
| 1.5 | 0.065 |
| 1.9 | 0.050 |
| 2.2 | 0.050 |
| 2.4 | 0.050 |
| 2.6 | 0.050 |
| 2.8 | 0.050 |
| 2.9 | 0.050 |
| 3.2 | 0.055 |
| 3.6 | 0.060 |
| 3.7 | 0.065 |
| 3.8 | 0.070 |
| 3.9 | 0.080 |
| 4.0 | 0.090 |
| 4.1 | 0.095 |

In a typical implantable drug delivery system, inlet port 20 of valve 10 would be connected to a pressurized supply of the drug, and the valve outlet port 18 would be connected by suitable means to the point of delivery in the patient.

It is therefore apparent that the present invention accomplishes its intended objects. While an embodiment of the present invention has been described in detail, this is for purpose of illustration, not limitation.

We claim:

1. An electromagnetic valve comprising:
   (a) a housing including a fluid containing region having first and second chambers and first and second ports in fluid communication with said first and second chambers, respectively;
   (b) electromagnet means carried by said housing and located externally of said fluid containing region;

(c) barrier means of fluid-impervious material for isolating said electromagnet means from said fluid containing region of said housing;

(d) an armature movably positioned in said fluid containing region of said housing and having a pole portion located for magnetic attraction by said electromagnet means and located between said first and second chambers and having a valve portion located for opening and closing one of said ports to place said ports in fluid communication through said fluid containing region of said housing in one control state of said valve and to block fluid communication between said ports through said fluid containing region of said housing in another control state of said valve;

(e) a body of magnetically permeable material in said housing fluid containing region between said first and second chambers, said body having a passage therethrough for receiving said armature pole portion in a movable, close-fitting relation whereby said armature moves in said body, said body having a fluid passage therein in fluid communication with said first and second chambers and separate from said armature pole portion receiving passage to allow fluid in said region to flow through said body between said first and second chambers; and (f) means for defining a magnetic circuit including said electromagnet means, said body, the included portions of said barrier means between said electromagnet means and said body, said armature pole portion and a gap between said pole portion and said electromagnet means located in said fluid containing region of said housing and external to said electromagnet means for closing said gap in response to electrical energization of said electromagnet to move said armature and change the control state of said valve.

2. A valve according to claim 1, further including biasing means operatively engaging said armature for urging said armature to a rest position placing said valve in one of said control states.

3. A valve according to claim 1, wherein said barrier means comprises a thin planar plate of metal and said housing and said electromagnet means are in contact with opposite surfaces of said plate.

4. A valve according to claim 1, wherein said passage in said body has an axial length and an inner surface, said armature pole portion has an outer surface spaced from said inner surface of said passage over a given length thereby defining an effective air gap therebetween and wherein said axial length of said passage in said body is relatively large as compared to said given length of said space between said inner surface of said passage and said outer surface of said armature pole portion to minimize said effective air gap defined therebetween and introduced in said magnetic circuit.

5. A valve according to claim 1, wherein said armature pole portion has a pole face disposed in a plane substantially perpendicular to the direction of movement of said armature, said pole face being located to define said gap with said electromagnet means, said pole face being of relatively large area.

6. A valve according to claim 1, wherein said barrier means comprises a thin plate of metal compatible with fluid in said fluid-containing region of said housing, said plate having opposite surfaces, said electromagnet means includes a housing of magnetically permeable material having an end face contacting one of said surfaces of said plate, and said body of magnetically permeable material having an end face contacting the other of said surfaces of said plate.

7. A valve according to claim 6, wherein the areas of contact of said end faces of said electromagnet housing and said body with said surfaces of said plate are of sufficient size to minimize the effective air gap introduced by said plate in said magnetic circuit.

8. A valve according to claim 1, wherein said electromagnet means comprises a coil wound on a spool within a housing, said electromagnet housing and said valve housing being located on a common axis, and said spool having a relatively small diameter.

9. A valve according to claim 1, wherein each of said body and armature pole portion has an outer surface and is provided with a layer on said outer surface thereof of a material which enhances compatibility of of fluid in said fluid containing region of said housing with said outer surfaces.

10. A valve according to claims 1 or 9, wherein said armature pole portion is provided with an exterior coating of a fluoropolymer material.

11. A valve according to claim 1, wherein said armature comprises a shaft and an enlarged body on one end of said shaft, said body being of magnetically permeable material and terminating in a pole face disposed substantially perpendicular to the axis of said shaft, the cross-sectional area of said pole face being significantly larger than the cross-sectional area of said shaft, said body and shaft being connected together through a bushing of fluoropolymer material.

12. A valve according to claim 1, wherein said housing is elongated having a longitudinal axis, said armature being positioned for movement along said housing longitudinal axis, said fluid containing region of said housing and said electromagnet means being in axially-spaced relation along said housing longitudinal axis, and said barrier means comprises a thin plate of metal compatible with fluid in said fluid containing region of said housing fixed between and providing an hermetic seal between said electromagnet means and said fluid containing region of said housing.

13. A valve according to claim 12, wherein one of said ports is in fluid communication with a chamber defined between said barrier plate and said body, said armature pole portion moves in said chamber and has a pole face on the end thereof disposed toward said barrier plate, and said gap is defined between said armature pole face and said barrier plate, whereby as said gap is reduced during energization of said electromagnet means causing movement of said armature pole face toward said barrier plate said armature valve portion opens the other of said ports.

14. A valve according to claim 12, wherein said electromagnet means includes a housing of magnetically permeable material having an end face contacting one surface of said barrier plate, said body has an end face contacting the other surface of said plate, and the areas of contact of said end faces of said electromagnet housing and said body with said surface of said plate are of sufficient size to minimize the effective air gap introduced by said plate in said magnetic circuit.

15. A valve according to claim 12, wherein said passage in said body has an axial length and an inner surface, said armature pole portion has an outer surface spaced from said inner surface of said passage over a given length thereby defining an effective air gap therebetween and wherein said axial length of said passage in said body is relatively long as compared to said given length of said space between said inner surface of said passage and said outer surface of said armature pole portion to minimize said effective air gap defined therebetween and introduced in said magnetic circuit.

16. In an electromagnetic valve including a housing having an interior fluid containing region including first and second chambers, first and second ports in fluid communication with said first and second chambers, respectively, electromagnet means carried by said housing and located external to said fluid containing region of said housing, and an armature positioned in said fluid containing region of said housing having a pole portion located between said first and second chambers for magnetic attraction by said electromagnet means causing movement of said armature for opening and closing one of said ports, the improvement comprising:
(a) barrier means of fluid-impervious material separating said electromagnet means and said fluid containing region of said housing;
(b) a body of magnetically permeable material in said housing fluid containing region between said first and second chambers and having a passage therethrough for receiving said armature pole portion in a movable, close-fitting relation, said body having a fluid passage therein in fluid communication with said first and second chambers and separate from said armature pole portion receiving passage to allow fluid in said region to flow through said body between said first and second chambers; and
(c) means for defining a magnetic circuit including said electromagnet means, said body, the included portions of said barrier means between said electromagnet means and said body, said armature pole portion and a gap in said fluid containing region of said housing between said armature pole portion and said electromagnet means for moving said armature toward said electromagnet means to close said gap in response to electrical energization of said electomagnet means.

17. An improved electromagnetic valve according to claim 16, wherein said barrier means comprises a thin metal plate fixed between and providing an hermetic seal between said electromagnet and said fluid containing region of said housing and wherein said electromagnet means includes a housing of magnetically permeable material having an end face contacting one surface of said barrier plate, said body has an end face contacting the other surface of said plate, and the areas of contact of said end faces of said electromagnet housing and said body with said surface of said plate are of sufficient size to minimize the effective air gap introduced by said plate in said magnetic circuit.

18. A valve according to claim 16, wherein said passage in said body has an axial length and an inner surface, said armature pole portion has an outer surface spaced from said inner surface of said passage over a given length thereby defining an effective air gap therebetween and wherein said axial length of said passage in said body is relatively long as compared to said given length of said space between said inner surface of said passage and said outer surface of said armature pole portion to minimize said effective air gap defined therebetween and introduced in said magnetic circuit.

19. An electromagnetic valve comprising:
(a) a housing including a fluid containing region and first and second ports in fluid communication with said region, said housing being elongated and having an end;
(b) electromagnet means carried by said housing and located externally of said fluid containing region, said electromagnet means being elongated and having an end;
(c) barrier means of fluid-impervious material for isolating said electromagnet means from said fluid containing region of said housing;
(d) said housing and electromagnet means being positioned in end-to-end relation and said barrier means being located between said ends;
(e) an armature movably positioned in said fluid containing region of said housing and having a pole portion located for magnetic attraction by said electromagnet means and having a valve portion located for opening and closing one of said ports to place said ports in fluid communication through said fluid containing region of said housing in one control state of said valve and to block fluid communication between said ports through said fluid containing region of said housing in another control state of said valve;
(f) a body of magnetically permeable material in said housing fluid containing region between said first and second ports, said body having a passage therethrough for receiving said armature pole portion in a movable, close-fitting relation whereby said armature moves in said body; and
(g) means for defining a magnetic circuit including said electromagnet means, said body, the included portions of said barrier means between said electromagnet means and said body, said armature pole portion and a gap between said pole portion and said electromagnet means located in said fluid containing region of said housing and external to said electromagnet means for closing said gap in response to electrical energization of said electromagnet to move said armature and change the control state of said valve.

20. A valve according to claim 19, wherein said barrier means comprises a thin planar plate of metal and said housing and said electromagnet means are in contact with opposite surface of said plate.

* * * * *